United States Patent [19]

Bommarito

[11] Patent Number: 5,290,250
[45] Date of Patent: Mar. 1, 1994

[54] FEEDING TUBE ADAPTER

[76] Inventor: Alexander A. Bommarito, 12555 W. Freeland Rd., Freeland, Mich. 48623

[21] Appl. No.: 976,573

[22] Filed: Nov. 16, 1992

Related U.S. Application Data

[63] Continuation-in-part of Ser. No. 844,247, Mar. 2, 1992, abandoned, which is a continuation-in-part of Ser. No. 688,838, Apr. 22, 1991, Pat. No. 5,102,396.

[51] Int. Cl.⁵ .............................................. A61M 5/32
[52] U.S. Cl. ....................................................... 604/175
[58] Field of Search ................ 604/175, 174, 283, 284

[56] References Cited

U.S. PATENT DOCUMENTS

| | | | |
|---|---|---|---|
| 3,153,415 | 10/1964 | Sheridan | 604/283 X |
| 3,721,231 | 3/1973 | Hubert | 604/283 X |
| 4,333,455 | 6/1982 | Bodicky | 604/284 X |
| 4,534,760 | 8/1985 | Raible | 604/175 |
| 4,534,761 | 8/1985 | Raible | 604/175 |
| 4,629,455 | 12/1986 | Kanno | 604/283 X |
| 4,878,900 | 11/1989 | Sundt | 604/283 X |
| 4,886,501 | 12/1989 | Johnston et al. | 604/175 |
| 4,895,561 | 1/1990 | Mahurkar | 604/283 X |
| 5,041,085 | 8/1991 | Osborne et al. | 604/283 X |
| 5,074,846 | 12/1991 | Clegg et al. | 604/283 X |
| 5,102,396 | 4/1992 | Bommarito | 604/174 X |
| 5,129,887 | 7/1992 | Euteneuer et al. | 604/283 X |

*Primary Examiner*—Gene Mancene
*Assistant Examiner*—Jeffrey A. Smith
*Attorney, Agent, or Firm*—Merlin B. Davey

[57] ABSTRACT

The present invention provides a feeding tube adapter for enteral feeding tubes that comprises a central passageway having an exit port having an inside diameter smaller than the exit port inside diameter of an enteral feeding tube and constructed to provide a Venturi effect on material passing through the adapter thereby inhibiting blockage when feeding formulas or medications are infused therein. The adapter is advantageously constructed in the form of a Y-Port for ease of irrigating.

3 Claims, 1 Drawing Sheet

FEEDING TUBE ADAPTER

CROSS REFERENCE TO RELATED APPLICATIONS

This application is a continuation-in-part of U.S. patent application Ser. No. 844,247 filed Mar. 2, 1992, and now abandoned, which is a continuation-in-part of U.S. patent application Ser. No. 688,838 filed Apr. 22, 1991, now U.S. Pat. No. 5,102,396 issued Apr. 7, 1992.

BACKGROUND OF THE INVENTION

Historically, Studley was among the first to associate nutritional status and disease outcome. In 1936, this pioneering investigator made the classic observation that marked weight loss prior to peptic ulcer surgery resulted in a higher post-operative mortality rate relative to weight-stable patients. Modern health care workers have identified weight loss as a major determinant of prognosis in many disease states.

Total health care is contingent upon sound nutritional status. Practicing physicians and physician extenders evaluating the clinical and nutritional status of their patients should be able to implement an effective feeding program when needed. The wide range of nutritional preparations, catheters and feeding tubes available makes it possible to meet the differing requirements of varying pathological states, either accompanying or causing malnutrition.

The enteral route is a primary means of improving nutritional status in most patients. It is simple, economical and tolerated well in most patients. Optimal enteral feeding requirements can be achieved with the large number of enteral formulas available.

Formulas for enteral use can be subdivided into three basic types: elemental, polymeric, and modular. All of the enteral formulas differ in content and source of nitrogen, carbohydrate, fat and other nutrients, osmolality, taste, residue and expense. The formula components are either premixed by the manufacturer, or added together by the nutritionist shortly before administration. All formulas have the potential to have undissolved, condensed, coagulated, amalgamated, intermixed solids resulting in thickening and enteral tube clogging.

Obstruction of enteral feeding tubes is also precepitated by medications added to feeding formulas or administered via the feeding tube. A major problem is undissolved medications being forced down feeding tubes. The increased cost of injectable or liquid forms of medications and the accessibility to oral tablets is seen as the reason for this ongoing problem.

Feeding tube design has also been associated with higher occurrence of clogging. The small caliber feeding tubes are frequently occluded by feedings and/or medications. The addition of an irrigation port can lower the work to flush the feeding tube and may result in a reduction in obstruction. Medical grade components of the tubes, polyurethane, polyvinylchloride, silicone, etc. do not seem to make a difference in occlusion rates. Large exit ports have been added with claimed advantages, but obstructed enteral feeding tubes is still a major problem. Standard feeding systems provide high rates of feeding in the range of 800 to 1200 ml. per hour. These rates are adjusted with a clamp or pump in normal patient feeding. In jejunal feeding high rates are not desirable and the standard feeding equipment is not advantageously employed.

The added cost of a new tube, nursing time, and x-ray; possible complications of the tube placement; and concern about interruption of feeding to the patient have provided the impetus for developing new devices and methods to clean and open clogged feeding tubes and now to help prevent obstruction of feeding tubes.

SUMMARY OF THE INVENTION

The present invention comprises an adapter for enteral feeding tubes, said adapter having an input end and a discharge end, said discharge end being constructed to securely and releasably engage a feeding tube input port, said adapter further comprising a central passageway constructed to provide a Venturi effect on material passing through said adapter, said central passageway having an exit port inside diameter smaller than the exit port inside diameter of the enteral feeding tube, thereby inhibiting blockage when feeding formulas or medications are infused therein. The adapter of this invention advantageously comprises a Y-port for flushing and universal formula administration. The adapter of this invention provides flow rate control, reduces catheter blockage from undissolved medications and feeding formulas and provides a secure catheter connection to prevent leaks and unintended removal with easy detachment when intended for trapped undissolved matter irrigation.

DETAILED DESCRIPTION OF THE INVENTION

The adapter of the present invention advantageously has from about an 8 Fr. to about a 2-6 Fr., preferably about 4 Fr., inside diameter near the discharge end to stop occlusion of the common feeding tube sizes. (A French unit, herein Fr., is approximately 0.013" as known in the art.) The central passageway generally is uniformly tapering from the larger size (8 Fr.) to the small size (2-6 Fr.) to provide a venturi effect which helps prevent occlusion or blockage. Other constructions, such as the provision of constricted areas in the tube, to provide a venturi effect may be employed if desired. The outside diameter of the adapter of this invention is advantageously from 6-8 Fr. to 30-40 Fr. to fit most feeding tube ends.

The adapter of this invention can be made of a number of medical grade materials, but such materials must have a friction fit or a high adhesive force of attachment between adapter and feeding tube port or catheter. The adhesive force of attachment between adapter and catheter is at least 2 lbs. and preferably at least 4 lbs., that is, a force of at least 2-4 lbs. is required to remove the catheter from the adapter. The adapter, of course, can be screwed or snapped on also, but a friction fit is the preferred technique.

The adapter of the invention can be advantageously employed to reduce the fluid flow in the catheter by adjustment of the height of the feeding formula or head pressure. In addition, the construction of the adapter of this invention advantageously reduces fluid flow by about 75%, i.e., to maximum rates from about 200 to 300 ml. per hour. (Poisenille's Law states the flow rate of a liquid through a tube is proportional to the fourth power of the tube radius; thus, if the radius of the tube is doubled, the flow rate will be 16 times as great.)

The use of the adapter of the present invention with a jejunocath resulted in only one tube occlusion in thousands of patient days of use and no unintended removal problems or leaks. The high adhesive attaching force or the friction fit is released by direct pressure, such as squeezing, on the connection which allows for easy removal without harm to a feeding catheter.

A venturi force is placed on the feeding formula when it has to flow from a larger to a smaller bore size. This effect has been noted in rivers and streams where you see clean clear areas with narrowing and an increase in water current. This effect also assists in the dissolution of medications when administered via the adapter. Finally, the irrigation of fluids via the adapter gives a higher force of irrigation resulting in less tube occlusion problems.

BRIEF DESCRIPTION OF THE DRAWING

The invention is further illustrated by the partial sectioned view of FIG. 1.

DETAILED DESCRIPTION OF THE DRAWING

Figure 1:
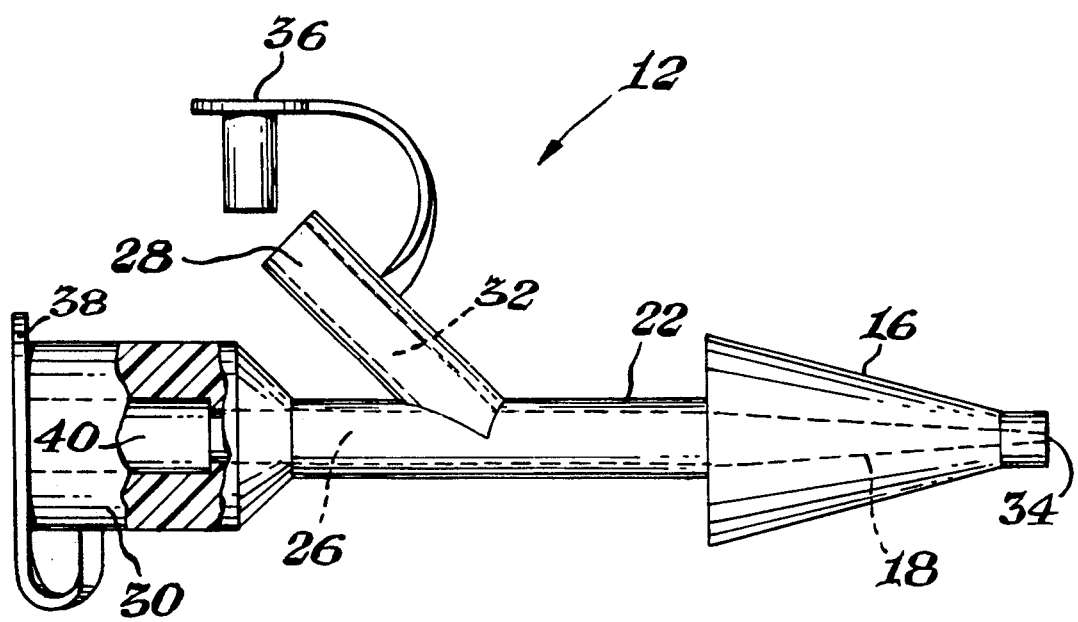

In the drawing, adapter (12) is shown in partially sectioned view and is seen to have a tapered discharge end (16), a tubular portion (22) connecting said discharge end (16) to an input end (30). Tube (28) is affixed to tubular portion (22) with passageway (32) of tube (28) being in operative communication with passageway (26) of tubular portion (22). Passageway (18) of discharge end (16) is seen to taper toward feed port (34). Caps (36) and (38) may be employed to close tube (28) and input end (30) respectively. Passageway (18) is designed to provide a Venturi effect. This is accomplished by tapering, as shown, although other designs may be employed, such as, for example, providing one or more constrictions in said passageway. The surface of discharge end (16) may be roughened or corrugated to provide improved adhesion to a feeding tube or catheter.

Input end (30) is made of a soft or semi-rigid medical grade material, but a soft material, such as, for example, Silastic (Registered Trademark) by Dow Corning, Kraton (Registered Trademark) by Shell or polyurethane, is preferred. The remainder of adapter (12) is advantageously made of hard or semi-rigid medical grade materials such as, for example, rigid polyurethane, polycarbonate and polyvinyl chloride.

Passageway (40) of input end (30) advantageously has an inside diameter of about 20 Fr. Tubular portion (22) advantageously has an outside diameter of about 20 Fr. and passageway (26) advantageously has an inside diameter of about 14 Fr. Passageway (18) tapers from an inlet of from about 14 Fr. to an outlet of from about 2-6 Fr., preferably about 4 Fr. Passageway (32), employed for irrigation or washing, advantageously has an inside diameter of about 12 Fr. and an outside diameter of about 20 Fr.

The soft input portion of the Y-Port is much better for patients' comfort and the snug fit of medical devices needed for care. The discharge portion of the adapter is advantageously made of a hard or rigid material to stop undissolved matter and act as a valve. It is also desirable for the friction fit or adhesive force to secure a solid connection to a feeding tube or catheter.

A major advantage of the adapter of this invention is that it serves to reduce blockage of surgically placed feeding or medication tubes. This is accomplished with the size and change in size over a short distance, i.e., a Venturi effect is created thereby increasing the emulsion stability coming out of, for example, the 4 Fr. end of a feeding or exit port (34) into, for example, an 8 Fr. enteral feeding tube and inhibiting blockage. Since the inside diameter of the feed port (34) is smaller than the inside diameter of the enteral feeding tube exit port, the adapter of this invention prevents blockage of the feeding tube by undissolved medications and feeding formulas. Under pressure feeding formulas will be reemulsified. Small hard rock-like insolubles will not pass the 4 Fr. feeding port and can be washed out with ease, by removal of the adapter from the feeding tube. The last advantage with the small adapter is to slow the rate of feeding. If enteral feedings are administered too fast a dumping syndrome can result. The rate of feeding will vary with the viscosity of the liquid formula diet and the head pressure or height of the feeding bag. Maximum rates are of the normal rate seen with common feeding formulas with a range of 15-25% and rates can be set at a safe level by control of the head pressure (adjusting of the feeding bag height) on set up. This eliminates the potential problem of feeding too fast and need for a feeding pump.

Various modifications may be made in the present invention without departing from the spirit or scope thereof as will be understood by those skilled in the art.

I claim:

1. An adapter for enteral feeding lubes, said adapter having an input, end and a discharge end, said discharge end being adapted to securely and releasably engage a feeding tube input port with a friction fit having anadhesive force of at least 2 pounds and said adapter comprising a central passageway leading from said input end to said discharge end said central passageway having an inside diameter of from about 2-6 Fr. at said discharge end thereby inhibiting blockages of said enteral feeding tube by undissolved matter and being constructed to provide a Venturi effect on material passing through said passageway thereby inhibiting blockage when soluble feeding formulas and medications are infused therein, said input end of said adapter being constructed of a material selected from the group consisting of soft and semi-rigid medical grade materials and said discharge end of said adapter being constructed of a material selected from the group consisting of hard and semi-rigid medical grade materials thereby inhibiting the passage of undissolved portions of feeding formulas and medications and wherein said friction fit permits easy removal of said adapter from said feeding tube input port by direct pressure.

2. Adapter of claim 1 wherein the inside diameter of said central passageway at said discharge end is smaller than the inside diameter of the exit port of said feeding tubes.

3. Adapter of claim 1 wherein said central passageway is generally uniformly tapered from about 14 Fr. to 2-6 Fr.

* * * * *